United States Patent [19]

Paul et al.

[11] 4,239,744

[45] Dec. 16, 1980

[54] RADIORECEPTOR ASSAY FOR BENZODIAZEPINES IN PLASMA AND OTHER BIOLOGICAL SPECIMENS

[75] Inventors: Steven M. Paul, Silver Spring; Phil Skolnick, Bethesda, both of Md.

[73] Assignee: United States of America, Washington, D.C.

[21] Appl. No.: 949,689

[22] Filed: Oct. 10, 1978

[51] Int. Cl.² .................... G01N 33/16; A61K 43/00
[52] U.S. Cl. ...................................... 424/1; 23/230 B; 424/12
[58] Field of Search ...................... 424/1, 12; 23/230 B

[56] References Cited

U.S. PATENT DOCUMENTS

| | | | |
|---|---|---|---|
| 3,901,654 | 8/1975 | Gross | 23/230 B |
| 4,083,948 | 4/1978 | Davis et al. | 424/1 |

OTHER PUBLICATIONS

Mohler et al., Lifesciences, vol. 20, No. 12, 1977, pp. 2101-2110.
Squires et al., Nature, vol. 266, Apr. 21, 1977, pp. 732-734.

*Primary Examiner*—Benjamin R. Padgett
*Assistant Examiner*—Christine M. Nucker
*Attorney, Agent, or Firm*—Holman & Stern

[57] ABSTRACT

A rapid and sensitive radioreceptor assay for measuring benzodiazepines in plasma and other biological specimens is described. This method is based on the competition between [³H] diazepam or tritiated flunitrazepam and pharmacologically active benzodiazepines present in plasma, for binding sites on rat brain synaptosomal membranes. No interference is obtained with drug-free plasma or plasma samples containing high concentrations of other commonly used drugs. High correlations ($r = 0.98$; $p < 0.001$) were obtained between the "diazepam equivalents" measured in plasma using the radioreceptor assay and the levels of diazepam and N-demethyl diazepam obtained by gas-liquid chromatography. The radioreceptor assay is rapid, sensitive, specific, and requires no sophisticated equipment or methodology. It should therefore prove useful in monitoring blood benzodiazepine levels for both therapeutic and toxicologic purposes.

7 Claims, 1 Drawing Figure

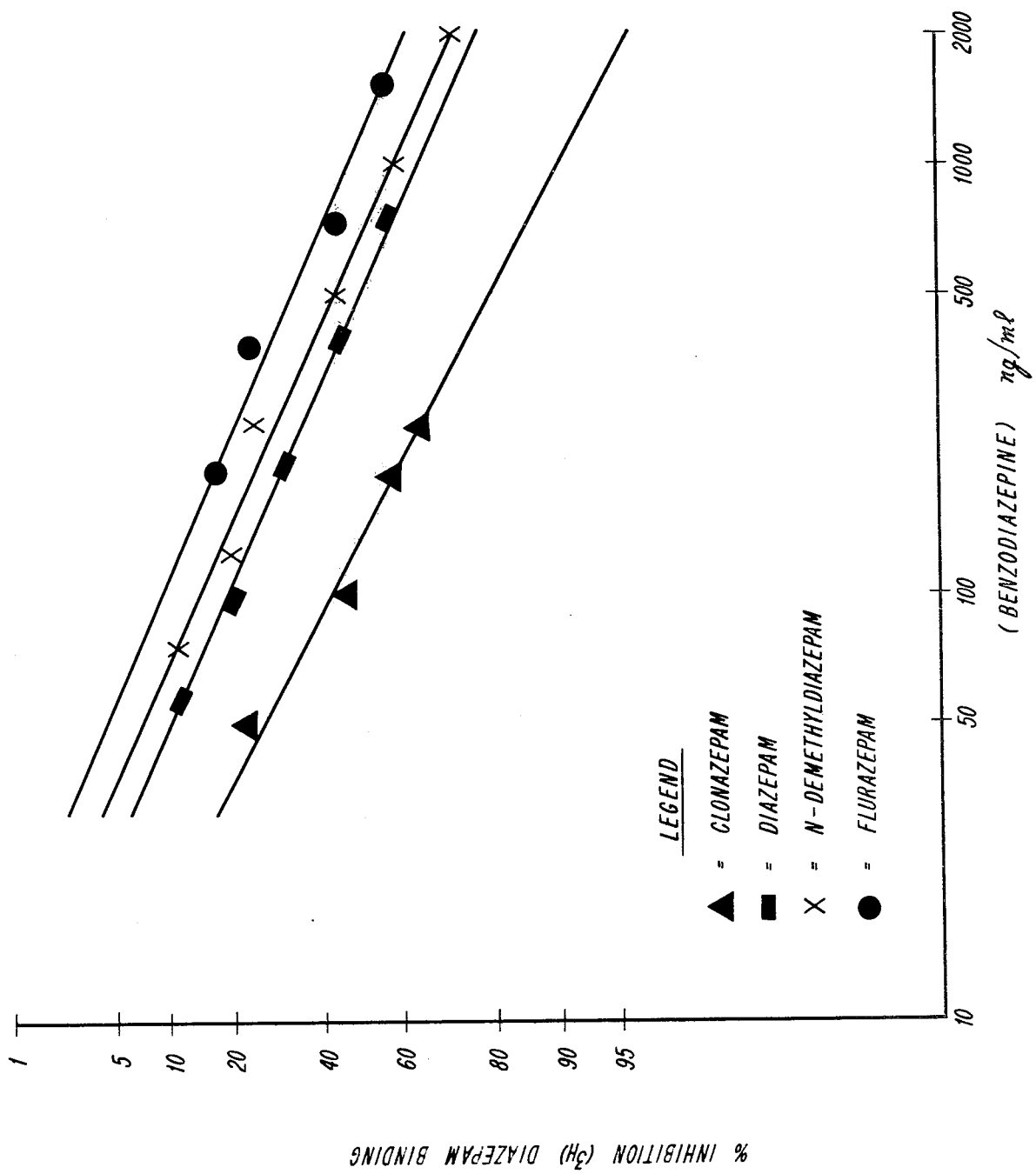

RADIORECEPTOR ASSAY FOR BENZODIAZEPINES IN PLASMA AND OTHER BIOLOGICAL SPECIMENS

This invention relates to radioreceptor assays of drugs and, in particular, to a rapid and sensitive radioreceptor assay for benzodiazepines in blood plasma and other biological specimens.

The benzodiazepines, which include diazepam, flurazepam, and chloridiazepoxide, comprise the most widely prescribed class of compounds in current therapeutic use (D. J. Greenblatt and R. I. Shader: *Benzodiazepines in Clinical Practice* 1974). Like many other drugs, the benzodiazepines show a wide range of blood levels among different individuals on a standard dose (ibid, Greenblatt et al). Further, there is some evidence indicating a relationship between the therapeutic and/or side effects of these drugs and their blood level (ibid, Greenblatt et al). These observations suggest that the clinical utility of these agents may be enhanced by blood level monitoring. Such monitoring is currently performed by gas-liquid chromatography, often coupled with electroncapture detection (GLC/EC) [J. A. Zingales: Diazepam metabolism during chronic medication, unbound fraction in plasma, erythrocytes and urine. *J. Chromatogr.* 75:55–78 (1975); D. M. Hailey: Chromatography of the 1,4-benzodiazepines. *J. Chromatogr.* 98: 527–568,1974; and M. Linnoila and F. Dorrity: Rapid gas chromatographic assay of serum diazepam, N-desmethyldiazepam, and N-desalkylfurazepam. *Acta pharmacol. et. toxicol.* 41: 458–464, 1977]. These methods, while sufficiently sensitive, have not achieved routine clinical use because of the sophisticated equipment required and the need for sample extraction prior to analysis. In addition, the extensive metabolism of benzodiazepines to a number of pharmacologically active metabolites has made monitoring of the parent drug alone or any one active metabolite of questionable significance, while measuring all metabolites is often too impractical for routine clinical use.

The recent identification of high affinity, stereospecific, binding sites for [$^3$H] diazepam in the mammalian central nervous system [C. Braestrup, A. Albrechtsen and R. F. Squires: High densities of benzodiazepine receptors in human cortical areas: *Nature* 269: 702–704, (1977), and H. Mohler and T. Okada: Benzodiazepine receptor: demonstration in the central nervous system. *Science* 198: 849–851, (1977)], affords an alternative method for measuring plasma benzodiazepines which is simple, rapid, and requires little equipment beyond that which is already available in most clinical laboratories. These binding sites are specific for benzodiazepines (ibid, Braestrup et al and Mohler et al), and the inhibition of binding by other benzodiazepines is highly correlated with clinical potency (ibid, Braestrup et al and Mohler et al). Thus, the radioreceptor technique permits the simultaneous measurement of all of the benzodiazepine compounds which bind the receptor, and thus, provides a total estimate of all pharmacologically active forms of the drug—a distinct advantage over existing chromatographic techniques.

BRIEF DESCRIPTION OF THE DRAWING

The FIGURE shows a percent inhibition curve

In general, according to the invention, there is provided a radioreceptor assay method for determining the concentration of pharmacologically-active benzodiazepines, such as clonazepam, diazepam, N-demethyldiazepam, flurazepam, and chlordiazepoxide, and/or their pharmacologically-active metabolites, and/or mixtures thereof contained in a biological specimen selected from the group consisting of blood plasma, urine, cerebral spinal fluid, and saliva. This method comprises:

(a) diluting the biological specimen with distilled water;

(b) adding at least about 1 ml of a synaptosomal membranes suspension containing about from 0.5 to 5.0 mg of protein per ml of said synaptosomal membranes suspension, to the diluted biological specimen obtained in step (a);

(c) adding tritiated diazepam or tritiated flunitrazepam, each having a specific radioactivity of about from 10 to 100 Ci/mmol, to the mixture containing the synaptosomal membranes and the biological specimen obtained in step (b);

(d) incubating the radioactive mixture obtained in step (c) at a temperature of about from 0° C. to 4° C. for about from 15 to 60 minutes;

(e) terminating the incubation carried out in step (d) with a wash containing about 5 ml of ice-cold 50 nM Tris buffer at a pH of about 7.4;

(f) filtering the incubate obtained in step (e) to obtain a mass comprising the said synaptosomal membranes and the tritiated diazepam or flunitrazepam bound thereto retained in the filter;

(g) washing the filter and mass retained therein obtained in step (f) with about 5 ml of said ice-cold buffer, and drying (as by air-drying) the said filter and mass retained therein;

(h) suspending the dried filter and mass retained therein obtained in step (g) in a liquid scintillation fluor; and (i) measuring the radiation of said mass in the fluor of step (h) with a liquid scintillation counter from which measurements the concentration of the benzodiazepines or their pharmacologically-active metabolites present in the biological specimen are determined for therapeutic and toxicological purposes.

Although this general method is equally operable for determining low concentrations of the benzodiazepines or their metabolites for therapeutic purposes and high concentrations for toxicological purposes, the use for the latter purpose is preferred since the method is rapid, sensitive, and accurate in determining a high concentration of the drug, as in an overdose situation.

The above method may be modified for routine determinations of the concentrations of the benzodiazepines and/or their metabolites and/or their mixtures, where it is suspected or anticipated that such concentrations may be low, as for example, in the routine administration of these drugs for therapeutic purposes. Such modified method includes preliminary steps involving removing the protein from the biological specimen by means of perchloric acid and thereafter submitting the remaining protein-free material to essentially the same treatment as carried out in the general method described above. This modified procedure, which as in the general procedure set forth above, also provides a radioreceptor assay method for routinely determining the concentration, suspected or anticipated of being at a low level, of the pharmacologically-active benzodiazepines, their pharmacologically-active metabolites, and their mixtures, contained in a biological specimen selected from the group consisting of blood plasma, urine, cerebral spinal fluid, and saliva, for therapeutic purposes, is fully set forth hereinafter, and comprises:

(a) diluting the biological specimen with water;

(b) adding perchloric acid to the diluted biological specimen obtained in step (a) to obtain a mixture containing the protein of the biological specimen which is precipitated by said perchloric acid as well as the protein-free remainder of the biological specimen which is present as a supernatant liquid;

(c) separating the supernatant liquid containing the protein-free remainder of the biological specimen obtained in step (b) from the protein precipitate;

(d) diluting the supernatent liquid separated in step (c) with distilled water;

(e) adding at least about 1 ml of a synaptosomal membranes suspension, containing about from 0.5 to 5.0 mg of protein per ml of said synaptosomal membranes suspension, to the diluted supernatant liquid obtained in step (d);

(f) adding tritiated diazepam or tritiated flunitrazepam, each having a specific radioactivity of about from 10 to 100 Ci/mmol, to the mixture containing the synaptosomal membranes and the supernatant liquid obtained in step (e);

(g) incubating the radioactive mixture obtained in step (f) at a temperature of about from 0° C. to 4° C. for about from 15 to 60 minutes;

(h) terminating the incubation carried out in step (g) with a wash containing about 5 ml of ice-cold 50 mM Tris buffer at a pH of about 7.4;

(i) filtering the incubate obtained in step (h) to obtain a mass comprising the said synaptosomal membranes and the tritiated diazepam or flunitrazepam bound thereto retained in the filter;

(j) washing the filter and mass retained therein obtained in step (i) with about 5 ml of said ice-cold buffer, and drying (as by air drying) the said filter and mass retained therein;

(k) suspending the dried filter and mass retained therein obtained in step (j) in a liquid scintillation fluor; and (l) measuring the radiation of said mass in the fluor of step (k) with a liquid scintillation counter from which measurements the concentration of the benzodiazepines or their pharmacologically-active metabolites present in the biological specimen are determined for therapeutic purposes.

In this modified method, it is preferred that the biological specimen be diluted with water in the ratio of from 1:5 for 1:10 in step (a). It is also preferred that about 50 μl of the perchloric acid be mixed with about 1 ml of the diluted biological specimen to precipitate the protein in step (b). It is additionally preferred that the supernatant liquid be separated from the protein-free remainder of the biological specimen by microcentrifuging in step (c). It is further preferred that 25 μl of the supernatant liquid be diluted with 375 μl of distilled water in step (d). Finally, it is also preferred that the tritiated diazepam or tritiated flunitrazepam be added to the mixture containing the synaptosomal membranes and the supernatant liquid in the amount of about from 2.5 to 3 nM (nM=nanomolar) in step (f). This modified method is particularly applicable to the treatment of blood plasma.

This modified method, while preferred for carrying out routine determinations involving low concentrations of the said benzodiazepines, their metabolies, and their mixtures, may also be used for determining high concentrations of these drugs although its use for said purpose is not preferred.

The method of the invention is exemplified hereafter by the following description of the treatment of blood plasma (including its derivation from blood).

Blood samples to be assayed are drawn into heparinized tubes and the plasma then separated therefrom by centrifugation at 40° C. Two-hundred μl of plasma is then pipetted into microtubes, e.g., Eppendorf Microtubes (Brinkman Instruments, Westbury, N.Y.) and diluted 1:10 with water. Samples are mixed by inversion and the plasma precipitated with 50 μl of perchloric acid. The samples are then vortexed briefly and centrifuged in a microcentrifuge, e.g., an Eppendorf Microfuge (Brinkman Instruments, Westbury, N.Y.), for three minutes. Twenty-five μl of the clear supernatant is withdrawn and added to 375 μl of distilled water in 16×125 mm glass tubes. Assays are thereafter performed at 0°-4° C. as follows:

One ml of synaptosomal membranes (containing approximately 1 mg of protein) prepared from rat cerebral cortex [S. M. Paul and P. Skolnick *Science*, in press (1978)] and which can be stored at −20° C. for six months without loss of activity is then added and the incubation started by the addition of tritiated diazepam, e.g., 2.5 –3 nM[$^3$H]diazepam (Specific Radioactivity 79.8 Ci/mmol, New England Nuclear, Boston, Mass.). The incubation is terminated after 15 min with a 5 ml wash of ice-cold 50 nM Tris buffer (2-amino-2-hydroxymethyl-1,3-propanediol) at pH 7.4, and immediately filtered through Whatman GF/B filters in a filtering device, e.g., a Millepore filtering bank (Model 1225, Millipore Corp., Bedford, Mass.) The filters are immediately washed with an additional 5 ml of ice-cold buffer. The filters are airdried and suspended in a scintillation fluor, e.g., in 10 ml "Aquasol" (New England Nuclear, Boston, Mass.) and the radiation measured in a liquid scintillation counter, e.g., a Beckman LS-355 liquid scintillation counter.

Standard curves were constructed by adding known amounts of benzodiazepine to plasma, diluting the plasma (1:5 or 1:10) with water, and proceeding in an identical manner to unknown samples. Total binding of [$^3$H] diazepam to rat synaptosomal membranes was determined by diluting 200 μl of untreated plasma with 800 μl of water, precipitating with perchloric acid, and proceeding as described for unknown samples. Nonspecific binding was determined by replacing the distilled water in the incubation mixture with diazepam (0.12 mM) to a final concentration of 3 μM. The percent inhibition of specific binding by plasma samples is defined as:

$$1 - \left( \frac{\text{CPM sample} - \text{CPM non-specific}}{\text{CPM total} - \text{CPM non-specific}} \right) \times 100$$

Under these conditions, specific binding was greater than 90% of the total binding. A series of standard curves were generated by plotting the percent inhibition of [$^3$H]diazepam binding versus the plasma concentration of various benzodiazepines on log-probit paper (as shown in the accompanying sole figure of the drawing). The slope and intercept of these lines were determined by least mean squares regression analysis and the benzodiazepine concentrations in unknown plasma samples computed from these values. The recovery of [$^3$H] diazepam (50–800 ng/ml) added to plasma was 98.5 ±

3%, and was independent of the diazepam concentration.

In order to assess the validity of the radioreceptor technique, plasma levels of diazepam and N-demethyldiazepam were determined by gas-liquid chromatography (Linnoila et al, supra) and compared to values obtained by the radioreceptor method in plasma samples from baboons (Papio sp.) administered 2-4 mg/kg of diazepam. The results obtained are shown in the following Table 1:

TABLE I

Comparison of plasma levels of diazepam determined by radioreceptor techniques and GLC/EC.

| | Radioreceptor Assay "Diazepam Equilalents" | GLC/EC Assay | | GLC/EC Assay "Diazepam Equivalents, |
|---|---|---|---|---|
| Sample No. | (ng/ml) | Diazepam (ng/ml) | N-demethyldiazepam (ng/ml) | Calculated" (ng/ml) |
| 1 | 597 | 134 | 582 | 624 |
| 2 | 327 | 308 | 150 | 436 |
| 3 | 687 | 133 | 654 | 694 |
| 4 | 760 | 187 | 599 | 707 |
| 5 | 150 | 60 | 156 | 192 |
| 6 | 839 | 174 | 726 | 800 |
| 7 | 109 | 42 | 80 | 110 |
| 8 | 177 | 56 | 154 | 186 |
| 9 | 623 | 143 | 445 | 523 |
| 10 | 729 | 214 | 466 | 624 |
| 11 | 871 | 220 | 662 | 800 |

Note 1:
Values obtained by the radioreceptor technique represent the mean of triplicate determinations (SEM<5%).
Note 2:
The plasma "Diazepam Equivalents" of N-demethyldiazepam obtained by GLC/EC were calculated from the standard curve for N-demethyldiazepam (from the accompanying sole figure of the drawing) and added to the levels of diazepam obtained by GLC/EC to give "Diazepam Equivalents, Calculated". Correlation coefficient (r) = 0.98, p<.001.

A series of standard curves was generated for four benzodiazepines, namely, clonazepam, diazepam, N-demethyldiazepam, and flurazepam, by dissolving each of these benzodiazepines in plasma and carrying out the plasma assay thereof in triplicate according to the specific procedure described above. The curves obtained are illustrated in the accompanying sole figure of the drawing in which the relationship between the probit of percent inhibition of [$^3$H] diazepam binding (ordinate) and the logarithm of plasma benzodiazepine concentration in ng/ml (abcissa) was linear for each of the compounds examined. Clonazepam, the most potent benzodiazepine tested, could be reliably measured in plasma samples at concentrations of 10 ng/ml while flurazepam, the least potent compound tested, could be reliably measured at approximately 100 ng/ml, as may be seen from the figure. No inhibition of [$^3$H] diazepam binding was observed with drug-free plasma.

The specificity of the radioreceptor assay was determined by testing various commonly used drugs as inhibitors of [$^3$H] diazepam binding (R. F. Squires and C. Braestrup: Benzodiazepine Receptors in rat brain: Nature 266: 732-734, 1977) at concentrations well above those normally found in plasma. None of these commonly used drugs tested inhibited binding in plasma concentrations of up to 10 μg/ml -concentrations well above those expected even in cases of drug overdose. These drugs are listed in Table II following hereafter.

TABLE II

Commonly Used Drugs Not Affecting Radioreceptor Assay for Plasma Benzodiazepines.

| | |
|---|---|
| Haloperidol | Atropine |
| Fluphenazine | Isoniazid |
| Pargyline | Chlorimopramine |
| Epinephrine | Desipramine |
| Phenobarbital | Trihexyphenidyl |

TABLE II-continued

Commonly Used Drugs Not Affecting Radioreceptor Assay for Plasma Benzodiazepines.

The drugs were present in the plasma at a concentration of 10 μg/ml.

Intra-assay reliability, defined as the variability between triplicate determinations of the plasma sample within an assay, was less than 5%. Inter-assay reliability, defined as the variability of determinations of the same plasma sample between assays, was also less than 5%.

Since N-demethyldiazepam is about 85% as potent as the parent compound in inhibiting [$^3$H] diazepam binding (as shown in the figure of the drawing), a weighted average of the potencies of diazepam and N-demethyldiazepam is expressed as "Diazepam Equivalents, Calculated" (see Table I). These values were compared with the diazepam levels ("Diazepam Equivalents") obtained with the radioreceptor assay. A high correlation (r=0.98; p<0.001) was obtained between plasma levels of diazepam and N-demethyldiazepam determined by the GLC/EC and the values obtained with the radioreceptor technique.

As mentioned above, current methodology for the measurement of benzodiazepines in blood by gas-liquid chromatography with electron capture requires sample extraction with organic solvents and sophisticated equipment not usually available in the clinical laboratory. Although this method is sensitive, each benzodiazepine derivative and metabolite(s) measured requires an internal standardization which may necessitate different chromatographic conditions for effective separation. Such techniques are usually time consuming and the blood levels of metabolites obtained are often difficult to interpret (H. H. Dasberg, E. van der Kleijn, P. J. R. Guclen, and H. M. van Praag: Plasma concentration of diazepam, and its metabolite N-demethyldiazepam in relation to anxiolytic effect. Clin. Pharmacol. and Ther. 15: 473-483, 1974), relative to the effective levels of pharmacologically "active" benzodiazepine in blood.

The present invention provides a rapid and sensitive, radioreceptor assay for plasma benzodiazepines with several distinct advantages over currently employed GLC/EC techniques. The radioreceptor assay requires only one dilution of plasma followed by a simple precipitation technique, thus eliminating the need for solvent extraction. Little additional equipment is required other than that which is commonly available to most clinical laboratories. The radioreceptor technique is also rapid; one investigator can easily process more than two hundred samples daily. In the present investigation, computer analysis of the data was performed for statistical purposes; however for routine laboratory use, accurate determinations of plasma benzodiazepine concentrations can be obtained directly from log-probit paper.

Perhaps the greatest advantages of the radioreceptor technique is the estimation of "benzodiazepine equivalents", which gives an indication of the therapeutic level(s) of both parent compound(s) and metabolite(s), since only those compounds which are clinically active will complete with [$^3$H] diazepam for binding sites (Squires et al, supra). The excellent correlations (as shown in Table I) observed between the "Diazepam Equivalents" obtained using the radioreceptor assay and the levels of diazepam and N-demethyldiazepam found with GLC/EC clearly demonstrates the utility of this technique. The measurement of "benzodiazepine equivalents" may also facilitate clinical studies designed to determine whether a therapeutic threshold or window exists for the plasma concentration(s) of these drugs.

Since only benzodiazepoines will compete with [$^3$H] diazepam for binding sites (as shown in Table II), blood levels can be determined in patients ingesting a variety of drugs, even at very high doses. This should prove valuable in suspected cases of drug overdose and for rapid determination of blood benzodiazepine levels in an emergency situation. The use of the radioreceptor assay is further facilitated by the preparation of large quantities of synaptosomal membranes which can be frozen and stored for several weeks without a significant loss of binding activity (an observation of the present inventors.)

The radioreceptor assay described herein is rapid, sensitive, specific, and requires no sophisticated equipment or methodology. These characteristics favor the use of this technique as a standard procedure for determining blood levels of benzodiazepines in the clinical laboratory.

The synaptosomal membranes suspension described above is prepared as follows:

(a) homogenize rat brains in 20 volumes of ice-cold 0.32 M sucrose (using a Potter-Elvehjern homogenizer);

(b) centrifuge the resulting suspension obtained in step (a) at 1000×g for 10 minutes;

(c) centrifuge the supernatent obtained in step (b) at 20,000×g for 20 minutes; and (d) resuspend the pellet obtained in step (c) in 40 volumes of Tris buffer to a final protein concentration of approximately 1 mg/ml.

"Aquasol", mentioned above, is a liquid scintillation counting fluorophore that contains a detergent, such as Triton X-100. The ingredients are, roughly, 1 volume water2 volumes Triton X 100/4 volumes toluene/0.04% (wt/wt) 2,5-diphenyloxazole, and 0.01% 1,4bis [2(5-oxazolyl) benzene].

What is claimed is:

1. A radioreceptor assay method for routinely determining the concentration of pharmacologically-active benzodiazepines, their pharmacologically-active metabolites, and mixtures thereof contained in a biological specimen selected from the group consisting of blood plasma, urine, cerebral spinal fluid, and saliva comprising:

(a) diluting the biological specimen with water;

(b) adding perchloric acid to the diluted biological specimen obtained in step (a) to obtain a mixture containing the protein of the biological specimen which is precipitated by said perchloric acid as well as the protein-free remainder of the biological specimen which is present as a supernatant liquid;

(c) separating the supernatant liquid containing the protein-free remainder of the biological specimen obtained in step (b) from the protein precipitate;

(d) diluting the supernatant liquid separated in step (c) with distilled water;

(e) adding at least about 1 ml of a synaptosomal membranes suspension, containing about from 0.5 to 5.0 mg of protein per ml of said synaptosomal membranes suspension, to the diluted supernatant liquid obtained in step (d);

(f) adding tritiated diazepam or tritated flunitrazepam, each having a specific radioactivity of about from 10 to 100 Ci/mmol, to the mixture containing the synaptosomal membranes and the supernatant liquid obtained in step (e);

(g) incubating the radioactive mixture obtained in step (f) at a temperature of about from 0° C. to 4° C. for about from 15 to 60 minutes;

(h) terminating the incubation carried out in step (g) with a wash containing about 5 ml of icecold 50 nM Tris buffer at a pH of about 7.4;

(i) filtering the incubate obtained in step (h) to obtain a mass comprising the said synaptosomal membranes and the tritiated diazepam or flunitrazepam bound thereto retained in the filter;

(j) washing the filter and mass retained therein obtained in step (i) with about 5 ml of said ice-cold buffer, and drying the said filter and mass retained therein;

(k) suspending the dried filter and mass retained therein obtained in step (j) in a liquid scintillatioin fluor; and (l) measuring the radiation of said mass in the fluor of step (k) with a liquid scintillation counter from which measurements the concentratin of the benzodiazepines or their pharmacologically-active metabolites present in the biological specimen are determined.

2. The method of claim 1 wherein the biological specimen is diluted with water in the ratio of from 1:5 to 1:10 in step (a).

3. The method of claim 2 wherein about 50 μl of the perchloric acid is mixed with about 1 ml of the diluted biological specimen to precipitate the protein in step (b).

4. The method of claim 3 wherein the supernatant liquid is separated from the protein-free remainder of the biological specimen by microcentrifuging in step (c).

5. The method of claim 4 wherein 25 μl of the supernatent liquid is diluted with 375 μl of distilled water in step (d).

6. The method of claim 5 wherein the tritiated diazepam or tritiated flunitrazepam is added to the mixture containing the synaptosomal membranes and the supernatant liquid in the amount of about from 2.5 to 3 nM in step (f).

7. The method of claim 6 wherein the biological specimen is blood plasma.

* * * * *